United States Patent [19]
Thomassen

[11] Patent Number: 4,996,986
[45] Date of Patent: Mar. 5, 1991

[54] IMPLANTABLE MEDICAL DEVICE FOR STIMULATING A PHYSIOLOGICAL FUNCTION OF A LIVING BEING WITH ADJUSTABLE STIMULATION INTENSITY AND METHOD FOR ADJUSTING THE STIMULATION INTENSITY

[75] Inventor: Niels Thomassen, Espergaerde, Denmark

[73] Assignee: Siemens Aktiengesellschaft, Berlin and Munich, Fed. Rep. of Germany

[21] Appl. No.: 506,856

[22] Filed: Apr. 9, 1990

[30] Foreign Application Priority Data

Apr. 12, 1989 [EP]  European Pat. Off. ........ 89106520.3

[51] Int. Cl.⁵ ............................................. A61N 1/365
[52] U.S. Cl. ............................................. 128/419.0 PG
[58] Field of Search ................................... 128/419 PG

[56] References Cited
U.S. PATENT DOCUMENTS 4,856,522 8/1989 Hansen ...................... 128/419.0 PG
4,856,523 8/1989 Sholder et al. ............ 128/419.0 PG Primary Examiner—William E. Kamm
Attorney, Agent, or Firm—Hill, Van Santen, Steadman & Simpson

[57] ABSTRACT

An implantable device for stimulating a physiological function of a living being with a stimulation intensity calculated/determined in view of the physical activity of the living being, wherein the spontaneous intensity of the physiological function is measured during various phases of spontaneous activity of the physiological function and the measured spontaneous intensity is compared to the calculated stimulation intensity, duration between the measured spontaneous intensity and calculated stimulation intensity causing corrections in an algorithm used to calculate the stimulation intensity.

4 Claims, 1 Drawing Sheet

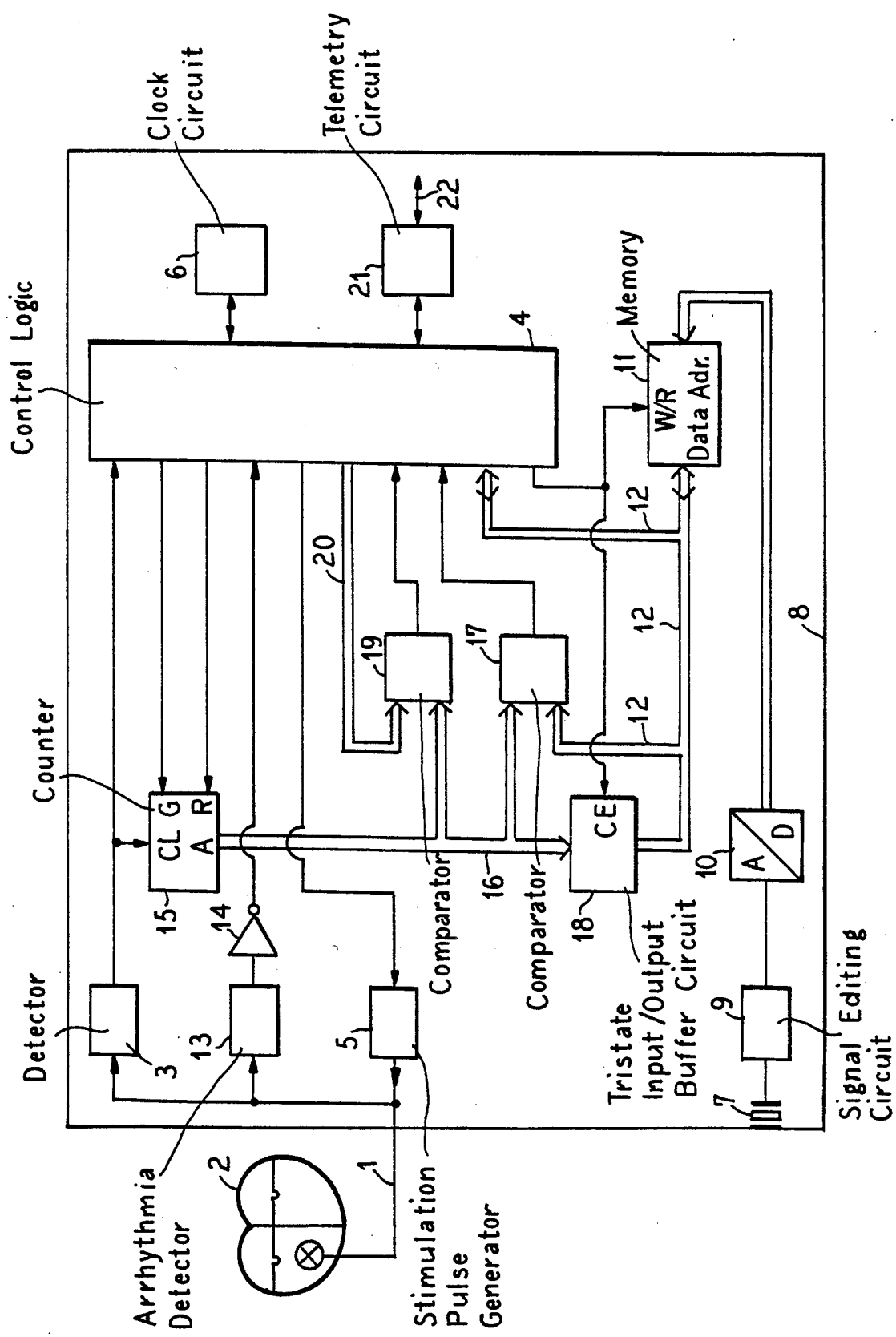

IMPLANTABLE MEDICAL DEVICE FOR STIMULATING A PHYSIOLOGICAL FUNCTION OF A LIVING BEING WITH ADJUSTABLE STIMULATION INTENSITY AND METHOD FOR ADJUSTING THE STIMULATION INTENSITY

BACKGROUND OF THE INVENTION

The invention is directed to medical devices implantable into the body of a living being having means for stimulating a physiological function of the being with adjustable stimulation intensity, comprising a sensor for forming a signal corresponding to the physical activity of the living being, means for implementing an algorithm for calculating a stimulation intensity adapted to the physical activity of the living being, and adjustment means that sets the stimulation intensity in view of the algorithm. The invention is also directed to a method for adjusting the stimulation intensity of the implantable device.

As used herein, the term "stimulation intensity" is understood to be comprehensive and to include duration, frequency, repetition rate, amplitude, etc. with which, e.g., means for stimulation are activated. Thus, the term "stimulation intensity" means any combination of the above-listed parameters.

Implantable medical devices of the type described above allow a living being, in whom they are implanted, to lead a normal life insofar as possible by providing necessary stimulation of a malfunctioning physiological function. The stimulation is provided with an intensity that depends upon the physical activity of the living being, the stimulation intensity corresponding as much as possible to that intensity that would be present if the living being were not dependent upon the artificial stimulation of the physiological function by the implantable medical device.

In U.S. Pat. No. 4,428,378, the teachings of which are fully incorporated herein by reference, there is disclosed an implantable medical device of the type discussed above. The disclosed device is an implantable heart pacemaker. The device includes a piezo-electric pressure sensor integrated therein that registers mechanical vibrations in the body of the being arising from movement of the muscles and the like during physical activities of the being, these mechanical vibrations propagating as pressure waves, and that converts the vibrations into a correlated physical activity electrical signal. The stimulation intensity, i.e., the stimulation frequency with which the heart pacemaker stimulates the heart given the absence of natural heartbeats, is calculated with reference to the correlated physical activity. The calculation is made according to a predetermined algorithm. The stimulation intensity is then set via adjustment means.

The algorithm used is based on the characteristics of an average patient, on the average coupling relationships of the piezo-electric sensor to the body of the patient, and on the average manufacturing tolerances with respect to the heart pacemaker, particularly with respect to those components that are used in the formation of the electrical signal correlated to the physical activity. This means that the stimulation frequency that is set and calculated according to the algorithm only rarely coincides with the heartbeat frequency with which the heart of the patient would be at spontaneously given a physical activity. In the majority of cases, the stimulation frequency that is set for a defined physical activity can deviate greatly from the spontaneous heartbeat frequency that the patient would otherwise have experienced given the physical activity. Thus, it can occur that the calculated stimulation frequency can correspond well to the patient's requirements for a time following implementation of the heart pacemaker, but otherwise deviates more and more from the spontaneous heartbeat frequency with which the heart of the patient would beat due to, for example, tissue growing over the piezo-electric sensor.

SUMMARY OF THE INVENTION

The present invention provides an implantable device for artificially stimulating a physiological function of a living being wherein the stimulation intensity is made to correspond closely, if not exactly, to the natural stimulation intensity that would otherwise be present given normal physiological function. To that end, the invention provides an implantable device for artificial stimulation of a physiological function of a living being, wherein the artificial stimulation intensity is determined algorithmically in view of sensed activity of the being and wherein natural stimulation intensity is measured with respect to the activity to alter that algorithm used to determine the artificial stimulation intensity so that the artificial stimulation intensity is made to correspond closely, if not exactly, to the natural stimulation intensity that would otherwise be present during such activity given normal physiological function.

In an embodiment, the invention provides an implantable device for artificially stimulating a physiological function of a living being wherein the artificial stimulation intensity is determined algorithmically in view of sensed activity, including detector means for detecting phases of spontaneous activity of the physiological function; means for measuring the spontaneous intensity of the physiological function; means for comparing the spontaneous intensity measured during a phase of spontaneous activity of the physiological function to the artificial stimulation intensity determined during the phase of spontaneous activity; and means for altering the algorithm used to determine the artificial stimulation intensity to eliminate deviation between the artificial stimulation intensity and the measured spontaneous intensity.

The invention takes into consideration that the spontaneous natural stimulation intensity of the physiological function to be stimulated established for a defined physical activity of the physiological function is the stimulation intensity that is best suited to the requirements of the living being. When the physiological function must be artificially stimulated, the artificial stimulation intensity should correspond to the spontaneous natural stimulation intensity present for the same physically activity during phases of spontaneous activity of the physiological function.

In an embodiment, the invention provides that the algorithm used to calculate the artificial stimulation intensity is corrected, i.e., altered, so that the calculated artificial stimulation intensity corresponds to the spontaneous intensity of the physiological function in view of the physical activity. Thus, the physiological function is artificially stimulated with a stimulation intensity that largely, if not exactly, corresponds to that spontaneous natural stimulation intensity of the physiological function otherwise present given normal physiological function.

An advantage of the invention therefore is that deviations between natural and artificial stimulation intensities are eliminated, at least for the most part. Further, if and when the characteristics of the device change, (for example, due to age) the algorithm is altered to compensate for such changes. At the very most, undesirable deviations occur during relatively short time spans required for correcting, i.e., altering, the algorithm.

In an embodiment, means for implementing the algorithm comprises a function memory. It is therefore easy to implement and alter the algorithm since exchange of data stored in the function memory is all that is required. Moreover, the data stored in the function memory is extremely easily accessible. Thus, in an embodiment, the physical activity signal is digitized and the resulting digital data is used to address the function memory.

In an embodiment, the invention provides that a check is performed before a correction of the algorithm takes place to determine if the measured spontaneous intensity falls within defined limits. Performance of this check prevents physiological meaningless correction of the algorithm. For example, the limits can involve maximum or minimum stimulation intensity levels.

BRIEF DESCRIPTION OF THE FIGURE

The sole figure is a block diagram of a heart pacemaker.

DETAILED DESCRIPTION OF THE PRESENTLY PREFERRED EMBODIMENTS

In the figure there is illustrated a heart pacemaker constructed for implantation in the body of a living being, e.g., a human being. The heart pacemaker is designed to work in the VVI mode and, accordingly, communicates with a heart 2 of the living being via an electrode 1 introduced into a ventricle of the heart 2.

The electrode 1 supplies a signal corresponding to electrical activity of the heart 2 to the pacemaker. Within the pacemaker, the signal supplied by the electrode 1 is received by a detector 3. The detector 3 detects the occurrence of spontaneous heartbeats. When an event having a minimum amplitude corresponding to a natural heartbeat and/or when an event having a specific steepness that is typical of a natural heartbeat occurs in the signal corresponding to the electrical activity of the heart 2, the detector means 3 outputs a signal indicating the occurrence of a natural heartbeat to a control logic circuit 4.

The illustrated heart pacemaker also comprises a stimulation pulse generator 5 that is in communication with the control logic circuit 4 and can be activated by the control logic circuit 4 to output an electrical stimulation pulse for stimulating a heartbeat. The output of the stimulation pulse generator 5 is connected to the electrode 1. Thus, the electrode not only supplies the signal corresponding to the electrical activity of the heart 2 to the heart pacemaker but also conducts the stimulation pulses from the heart pacemaker to the heart 2.

The control logic circuit 4 always causes the stimulation pulse generator 5 to output a stimulation pulse when no natural heartbeat is detected by the detector means 3, after the expiration of a defined time interval (referred to as the base interval) following a natural heartbeat detected by the detector means 3 or a stimulation pulse output by the stimulation pulse generator 5. The heart pacemaker thus prevents the heartbeat frequency from dropping below a frequency corresponding to the base interval, since, as required, it stimulates heart activity with a stimulation frequency that corresponds to the base interval.

The duration of the base interval is calculated by the control logic circuit 4. To this end, the control logic circuit 4 counts off a defined plurality of clock pulses that are supplied to it by a clock generator 6, for example, a crystal oscillator.

In the case of the described heart pacemaker, the chronological duration of the base interval does not have a fixed value. On the contrary, the chronological duration of the base interval varies in view of the physical activity of the living being such that the stimulation frequency with which the heart pacemaker stimulates falls between an upper limit value, for example 150 pulses per minute, and a lower limit value, for example, 60 pulses per minute. Increasing physical activity of the living being will cause the stimulation frequency to increase from the lower limit to the upper limit.

Data corresponding to the stimulation limits can be stored in the control logic 4 as values representing stimulation pulses or heartbeats per minute. The heart pacemaker thus can simulate the dependency of the spontaneous heartbeat frequency on the physical activity by setting a stimulation frequency matched to the physical activity.

In order to be able to calculate the pacemaker stimulation frequency adapted to the physical activity or, respectively, the chronological duration of the base interval corresponding thereto, a piezo-electric pressure sensor 7 is provided that is connected to the wall of a housing 8 that surrounds the electronics of the heart pacemaker in hermetically tight fashion. During physical activities of the living being, mechanical vibrations in the body of the living being that arise due to the movement of the muscles and the like, propagate as pressure waves in the body of the living being and are registered by the pressure sensor 7 and converted into electrical signals. These signals, whose amplitudes increase with increasing physical activity, are supplied to a signal editing circuit 9 that filters and amplifies these signals.

An output signal of the signal editing circuit 9 is supplied to an analog-to-digital converter 10. The digital output signals thereof are in turn supplied to address inputs of a write/read memory, preferably a random access memory (RAM) 11 that normally operates in read mode. An input W/R of the RAM 11 serving the purpose of switching the RAM 11 from the write mode to read mode and vice versa is supplied with a corresponding signal by the control logic circuit 4.

Data input/outputs of the RAM 11 are connected to a data processing bus 12 via which, among other things, they are connected to the control logic 4.

The RAM 11 works as a function memory. To this end, data corresponding to the stimulation frequency, such as value representing the number of stimulation pulses or heartbeats per minute as in the case of the exemplary embodiment, and data corresponding to the duration of the base interval, are stored in the RAM 11 for defined values of the digital output data of the analog-to-digital converter 10 that respectively correspond to a defined physical activity of the patient. An algorithm for calculating a stimulation frequency adapted to the physical activity of the patient respectively existing is thus, so to speak, stored in the RAM 11 in the form of a function table.

The data stored in the RAM 11 that correspond to the respectively existing output data of the analog-to-digital converter 10 are supplied to the control logic circuit 4 that in turn calculates counts of plurality of clock pulses of the clock generator 6 in view of these data. The counts correspond to durations of the base interval adapted to the respective physical activities of the patient. It should be clear that the stimulation frequency, or, respectively, the chronological duration of the base interval that is established, changes according to the data stored in the RAM 11 matched to the physical activity of the life form.

In order to provide that the stimulation frequency set for a defined physical activity of the patient corresponds as exactly as possible to that heartbeat frequency with which the heart of the patient would spontaneously beat given the same physical activity, it is provided in the illustrated heart pacemaker that the spontaneous heartbeat frequency is measured during phases of spontaneous heart activity wherein the heart follows a sinue rhythm. The spontaneous heartbeat frequency measured during such a phase is compared to the pacemaker stimulation frequency for that phase. In the case of a deviation, the algorithm stored in the RAM 11 is automatically corrected so that the stimulation frequency calculated according to the algorithm at least essentially corresponds to the measured, spontaneous heartbeat frequency.

To this end, the signal corresponding to the electrical activity of the heart is supplied not only to the detector means 3, but also to an arrhythmia detector 13 that supplies an output signal when an arrhythmia is present. Such an arrhythmia detector is disclosed, for example, in U.S. Pat. No. 3,861,387, the teachings of which are fully incorporated herein by reference. The output signal of the arrhythmia detector 13 is supplied via an inverter 14 to the control logic circuit 4. The control circuit 4 thus always receives a signal when the heart beats spontaneously following the sinue rhythm.

A counter 15 is also present that serves for identifying the spontaneous heartbeat frequency during phases of spontaneous heart activity according to the sinue rhythm. To this end, a clock input CL of the counter 15 is connected to the output of the detector means 3. When a phase of spontaneous heart activity according to the sinue rhythm is detected, the control logic circuit 4 supplies a signal to a gate input G of the counter 15 for a defined chronological duration that the control logic 4 calculates by counting off a corresponding plurality of clock pulses of the clock generator, said signal effecting that the spontaneous heartbeats appearing during this chronological duration are counted. Corresponding data are then available at the end of the time interval at output A of the counter 15, these data indicating the spontaneous heartbeat frequency in heartbeats per minute, since the gate of the counter 15 is opened for one minute in the case of the exemplary embodiment.

The output data of the counter 15 are supplied via a data line 16 to one input of a digital comparator 17. The other input of the comparator 17 is supplied, via the data bus 12, with those data that correspond to that stimulation frequency that is stored in the RAM 11 for the digital output data of the analog-to-digital converter 10 that corresponds to the momentary physical activity of the living being and, consequently, would be set if a stimulation of the heart 2 were required. When the comparison at the end of the described counting event yields a deviation of the measured, spontaneous heartbeat frequency from the stimulation frequency stored in the RAM 11 for the momentary physical activity of the patient, the control logic 4 recognizes this with reference to the corresponding output signal of the comparator 17. In reference thereto, the control logic 4 switches the RAM 11 to write mode and connects the data line 16 to the data bus 12 via a tristate input/output buffer 18 having a suitable number of channels. A control input CE of the buffer 18 is connected to the W/R input of the RAM 11. In view of the foregoing, the data corresponding to the spontaneous heartbeat frequency measured with the counter 15 are written into the RAM 11 instead of the previously existing data. After the end of the write event, the control logic 4 switches RAM 11 back to read mode, disconnects the data line 16 from the data bus 12 with the circuit 18 and resets the counter 15 by supplying a pulse to reset input R of the counter 15.

Insofar as the output signal of the inverter 14 continues to indicate the presence of a phase of spontaneous heart activity according to the sinue rhythm, the control logic 4 restarts the procedures set forth above by supplying a corresponding signal to the gate input G of the counter 15.

It thus becomes clear that the data stored in the RAM 11 represents an algorithm for calculating a stimulation frequency adapted to the physical activity of the living being that is continuously adapted to the respective conditions. The stimulation frequency calculated according to the algorithm stored in the RAM 11 thus corresponds to the greatest possible degree to that heartbeat frequency with which the heart 2 would spontaneously beat.

When the comparison shows that the measured, spontaneous heartbeat frequency coincides to the stimulation frequency stored in the RAM 11 for the digital output data of the analog-to-digital converter 10 corresponding to the momentary physical activity of the patient, the control logic 4 resets the counter 15 by supplying a corresponding pulse to its reset input R. Further, the control logic 4 starts a new counting event by supplying a corresponding signal to the gate input G of the counter 15. A switching of the RAM 11 to write mode is omitted.

When a phase of spontaneous heart activity according to the sinue rhythm ends during one of the above-described counting events that serves the purpose of identifying the spontaneous heartbeat frequency, the counting event is aborted because the control logic 4 inhibits the gate input G of the counter 15 and resets the counter 15 by supplying a corresponding pulse to the reset input R thereof.

In the case of the described heart pacemaker, a further digital comparator 19 is provided having one input connected to the data line 16 so that data corresponding to the respectively measured, spontaneous heartbeat frequency are supplied to it. Data that correspond to the upper end or to the lower limit value between which the stimulation intensity can be set are supplied to the other input of the comparator 19 by the control logic 4 via a data line 20. Before the control logic 4 initiates the storing of a measured, spontaneous heartbeat in the RAM 11 in the way set forth above, a check is carried out via two successive comparison procedures with the comparator 19 to see whether the measured, spontaneous heartbeat frequency lies within the limits set by the upper and lower limit values of the stimulation frequency. When the measured spontaneous heartbeat frequency falls outside of the predefined range, the storing thereof is omitted, so that it is assured that no data that are physiologically meaningless or, respectively, inadmissible can be supplied to the RAM 11. Instead, a new counting event is started because the control logic first rests the counter 15 by supplying a corresponding pulse to its reset input R and then supplies the gate input G of the counter with a signal that initiates a new counting event.

As further illustrated, a telemetry circuit 21 is connected to the control logic 4 so that the heart pacemaker is able to bidirectionally exchange data with an external device (not shown), such as a programmer. This is indicated by the double arrow 22. There is thus the possibility of programming the heart pacemaker. For example, the upper and the lower limit value for the stimulation frequency can be input by the programmer via the telemetry circuit 21.

Insofar as, differing from the described heart pacemaker, the data supplied by the counter 15, the RAM 11 and the control logic 4 that refer to stimulation pulses or heartbeats per minute, as in the case of the exemplary embodiment, are not compatible with one another, these data cannot be directly supplied to the comparators 17 and 19. On the contrary, the compatibility of the data must first be produced with, for example, a calculating event carried out by the control logic 4.

Although the invention has been set forth with reference to a heart pacemaker, it can also be employed in other devices for stimulating a physiological function. In this case, but in heart pacemakers as will, the functions critical for the invention can also be realized in a fashion deviating from the exemplary embodiment set forth above. In particular, other sensor devices can be employed. Moreover, the means for implementing the algorithm for calculating the stimulation intensity adapted to the respective physical activity of the patient need not necessarily comprise a write/read memory 11.

I claim:

1. A medical device implantable into the body of a living being, comprising:
   (a) means for stimulating a physiological function of the living being with adjustable stimulation intensity;
   (b) detector means for detecting phases of spontaneous activity of the physiological function;
   (c) means connected to said detector means for measuring the spontaneous intensity of said physiological function during the phases of spontaneous activity;
   (d) sensor means forming a signal corresponding to the physical activity of the living being;
   (e) converting means connected to said sensor means and containing a variable allocation arrangement for converting said signal into a stimulation intensity correlating to the physical activity;
   (f) adjustment means connected to said means for stimulating and said means for converting for providing said means for stimulating with said converted stimulation intensity; and
   (g) means connected to said means for measuring, said adjustment means and said converting means for comparing said spontaneous intensity with said converted stimulation intensity during said phases of spontaneous activity, and, in case of a deviation, for adjusting said allocation arrangement to a conversion of said signal corresponding to the physical activity into a value of said stimulation intensity, which, at least essentially, corresponds to the measured spontaneous intensity.

2. The device of claim 1, wherein said allocation arrangement comprises a function memory in which the converted signals are stored in the form of a function table that contains defined values of the stimulation intensity for defined values of the signal of the sensor means, whereby the allocation arrangement is adjusted by replacing the existing defined value corresponding to the signal of the sensor means with the measured value of the spontaneous intensity.

3. A method for setting the stimulation intensity of a device for stimulating a physical function of a living being with a stimulation intensity adapted to the physical activity of the living being, comprising the steps of:
   (a) measuring a spontaneous intensity of the physiological function during phases of spontaneous activity of the physiological function;
   (b) sensing the physical activity and converting the sensed physical activity into a stimulation intensity corresponding to the sensed physical activity;
   (c) comparing the spontaneous intensity measured during a phase of spontaneous activity to the converted stimulation intensity corresponding to the sensed physical activity during the phase of spontaneous activity; and
   (d) altering the conversion of the sensed physical activity so that a converted stimulation intensity, converted by the altered conversion, at least essentially corresponds to the measured spontaneous intensity.

4. The method of claim 3, wherein the conversion is altered only if the measured spontaneous intensity falls between defined limits.

* * * * *